US008182730B2

(12) United States Patent
Ratnayake et al.

(10) Patent No.: US 8,182,730 B2
(45) Date of Patent: May 22, 2012

(54) METHOD FOR FORMING A CONCENTRATING DEVICE

(76) Inventors: Chitra Kumari Ratnayake, Yorba Linda, CA (US); Michael Paul Henry, Bardon (AU)

( * ) Notice: Subject to any disclaimer, the term of this patent is extended or adjusted under 35 U.S.C. 154(b) by 790 days.

(21) Appl. No.: 12/185,999

(22) Filed: Aug. 5, 2008

(65) Prior Publication Data

US 2009/0033002 A1 Feb. 5, 2009

Related U.S. Application Data

(63) Continuation of application No. 11/446,130, filed on Jun. 5, 2006, now abandoned.

(60) Provisional application No. 60/693,047, filed on Jun. 23, 2005.

(51) Int. Cl.
*B29C 39/10* (2006.01)

(52) U.S. Cl. .................................. 264/267; 264/347

(58) Field of Classification Search .................. None
See application file for complete search history.

(56) References Cited

U.S. PATENT DOCUMENTS

| | | | |
|---|---|---|---|
| 4,483,773 A | 11/1984 | Yang | |
| 4,675,300 A | 6/1987 | Zare et al. | |
| 4,793,920 A | 12/1988 | Cortes et al. | |
| 4,865,706 A | 9/1989 | Karger et al. | |
| 5,015,350 A | 5/1991 | Wiktorowicz | |
| 5,112,460 A | 5/1992 | Karger et al. | |
| 5,120,413 A | 6/1992 | Chen et al. | |
| 5,139,630 A | 8/1992 | Chen | |
| 5,145,567 A | 9/1992 | Hsieh et al. | |
| 5,164,055 A | 11/1992 | Dubrow | |
| 5,202,006 A | 4/1993 | Chen | |
| 5,202,010 A | 4/1993 | Guzman | |
| 5,222,092 A | 6/1993 | Hench et al. | |
| 5,259,939 A | 11/1993 | Chen | |
| 5,264,095 A | 11/1993 | Hseih et al. | |
| 5,264,101 A | 11/1993 | Demorest et al. | |
| 5,292,372 A | 3/1994 | Swaisgood et al. | |
| 5,292,416 A | 3/1994 | Novotny et al. | |
| 5,310,462 A | 5/1994 | Chen | |
| 5,320,730 A | 6/1994 | Ewing et al. | |
| 5,332,481 A | 7/1994 | Guttman | |
| 5,340,452 A | 8/1994 | Brenner et al. | |
| 5,348,658 A | 9/1994 | Fuchs et al. | |

(Continued)

FOREIGN PATENT DOCUMENTS

EP 0517370 A1 12/1992

(Continued)

OTHER PUBLICATIONS

Channer, et al., "Practical Evaluation of Sol-gel and Hydrothermal Fritting Technologies for Rapid Column Fabrication and its Application in Capillary Electrochromatography and Micro-Liquid Chromatography," *Chromatographia*, (Aug. 2003), vol. 58, No. 3/4, pp. 135-143.

(Continued)

*Primary Examiner* — Edmund H. Lee
(74) *Attorney, Agent, or Firm* — Kilpatrick Townsend & Stockton LLP

(57) ABSTRACT

The present invention relates to novel methods and apparatus for improving the sensitivity of capillary zone electrophoresis (CZE). The invention particularly concerns devices comprising a channel that contains an in-line sol-gel column to concentrate samples being subjected to capillary zone electrophoresis, and the use of such devices to enhance the sensitivity of capillary zone electrophoresis.

21 Claims, 11 Drawing Sheets

U.S. PATENT DOCUMENTS

| | | | |
|---|---|---|---|
| 5,364,520 | A | 11/1994 | Okuyama et al. |
| 5,370,777 | A | 12/1994 | Guttman et al. |
| 5,374,527 | A | 12/1994 | Grossman |
| 5,384,024 | A | 1/1995 | Moring et al. |
| 5,405,782 | A | 4/1995 | Kohn et al. |
| 5,421,980 | A | 6/1995 | Guttman |
| 5,423,966 | A | 6/1995 | Wiktorowicz |
| 5,453,382 | A | 9/1995 | Novotny et al. |
| 5,490,909 | A | 2/1996 | Wang et al. |
| 5,503,722 | A | 4/1996 | Guttman |
| 5,514,543 | A | 5/1996 | Grossman et al. |
| 5,534,123 | A | 7/1996 | Bashkin et al. |
| 5,545,302 | A | 8/1996 | Zhu et al. |
| 5,552,028 | A | 9/1996 | Madabhushi et al. |
| 5,567,292 | A | 10/1996 | Madabhushi et al. |
| 5,571,680 | A | 11/1996 | Chen |
| 5,580,016 | A | 12/1996 | Sarrine |
| 5,582,705 | A | 12/1996 | Yeung et al. |
| 5,593,559 | A | 1/1997 | Wiktorowicz |
| 5,599,433 | A | 2/1997 | Keo et al. |
| 5,665,216 | A | 9/1997 | Karger et al. |
| 5,695,626 | A | 12/1997 | Yeung et al. |
| 5,728,282 | A | 3/1998 | Bashkin et al. |
| 5,741,411 | A | 4/1998 | Yeung et al. |
| 5,753,094 | A | 5/1998 | Alter et al. |
| 5,766,435 | A | 6/1998 | Liao et al. |
| 5,770,029 | A | 6/1998 | Nelson et al. |
| 5,777,096 | A | 7/1998 | Grossman et al. |
| 5,800,692 | A | 9/1998 | Naylor et al. |
| 5,840,388 | A | 11/1998 | Karger et al. |
| 5,846,395 | A | 12/1998 | Sarrine et al. |
| 5,863,401 | A | 1/1999 | Chen |
| 5,891,313 | A | 4/1999 | Johnson et al. |
| 5,916,426 | A | 6/1999 | Madabhushi et al. |
| 5,948,227 | A | 9/1999 | Dubrow |
| 5,958,694 | A | 9/1999 | Nikiforov |
| 5,964,995 | A | 10/1999 | Nikiforov et al. |
| 5,976,336 | A | 11/1999 | Dubrow et al. |
| 5,989,399 | A | 11/1999 | Chu et al. |
| 5,999,681 | A | 12/1999 | Grabbe et al. |
| 6,001,230 | A | 12/1999 | Burolla |
| 6,001,232 | A | 12/1999 | Chu et al. |
| 6,007,690 | A | 12/1999 | Nelson et al. |
| 6,033,546 | A | 3/2000 | Ramsey |
| 6,042,710 | A | 3/2000 | Dubrow |
| 6,068,752 | A | 5/2000 | Dubrow et al. |
| 6,074,541 | A | 6/2000 | Srinivasan et al. |
| 6,074,542 | A | 6/2000 | Dolnik et al. |
| 6,074,827 | A | 6/2000 | Nelson et al. |
| 6,107,044 | A | 8/2000 | Nikiforov |
| 6,129,826 | A | 10/2000 | Nikiforov et al. |
| 6,136,187 | A | 10/2000 | Zare et al. |
| 6,153,073 | A | 11/2000 | Dubrow et al. |
| 6,235,175 | B1 | 5/2001 | Dubrow et al. |
| 6,274,089 | B1 | 8/2001 | Chow et al. |
| 6,306,273 | B1 | 10/2001 | Wainright et al. |
| 6,316,201 | B1 | 11/2001 | Nikiforov |
| 6,344,326 | B1 | 2/2002 | Nelson et al. |
| RE37,606 | E | 3/2002 | Guttman |
| 6,355,709 | B1 | 3/2002 | Madabhushi et al. |
| 6,358,385 | B1 | 3/2002 | Madabhushi et al. |
| 6,372,353 | B2 | 4/2002 | Karger et al. |
| 6,406,604 | B1 | 6/2002 | Guzman |
| 6,410,668 | B1 | 6/2002 | Chiari |
| 6,416,642 | B1 | 7/2002 | Alajoki et al. |
| 6,428,666 | B1 | 8/2002 | Singh et al. |
| 6,432,290 | B1 | 8/2002 | Harrison et al. |
| 6,436,646 | B1 | 8/2002 | Nikiforov |
| 6,440,284 | B1 | 8/2002 | Dubrow |
| 6,475,362 | B1 | 11/2002 | Gorfinkel et al. |
| 6,475,363 | B1 | 11/2002 | Ramsey |
| 6,613,525 | B2 | 9/2003 | Nelson et al. |
| 6,664,104 | B2 | 12/2003 | Pourahmadi et al. |
| 6,686,035 | B2 | 2/2004 | Jiang et al. |
| 6,695,009 | B2 | 2/2004 | Chien et al. |
| 6,759,126 | B1 | 7/2004 | Malik et al. |
| 6,764,817 | B1 | 7/2004 | Schneider |
| 6,770,201 | B2 | 8/2004 | Shepodd et al. |
| 6,787,016 | B2 | 9/2004 | Tan et al. |
| 2002/0029968 | A1 | 3/2002 | Tan et al. |
| 2002/0055184 | A1 | 5/2002 | Naylor et al. |
| 2002/0119482 | A1 | 8/2002 | Nelson et al. |
| 2003/0057092 | A1 | 3/2003 | Chien et al. |
| 2003/0217923 | A1 | 11/2003 | Harrison et al. |
| 2003/0224436 | A1 | 12/2003 | Nelson et al. |

FOREIGN PATENT DOCUMENTS

| | | | |
|---|---|---|---|
| EP | 0518475 | A1 | 12/1992 |
| WO | WO 9310258 | A1 | 5/1993 |
| WO | WO 9711363 | A1 | 9/1996 |

OTHER PUBLICATIONS

Cheong, Won Jo, "Metal Tubing/Frit with a Sintered Frit of Silica Particles and a Chromatography Column with Such Tubing/Frits," *Journal of Chromatography A.*, (2005), vol. 1066, pp. 231-237.

Foret, et al., "Capillary Electrophoresis: Present State of Art," *Electrophoresis* (1990), vol. 11, pp. 661-664.

Yu Yang, Ping He., "Studies on the Long-Term Thermal Stability of Stationary Phases in Subcritical Water Chromatography," *Journal of Chromatography A*, (2003), vol. 989, pp. 55-63.

Backhouse C.J. et al., "Improved Resolution With Microchip-Based Enhanced Field Inversion Electrophoresis," *Electrophoresis* 2003 24(11):1777-1786.

Bean S.R. et al., "Sodium Dodecyl Sulfate Capillary Electrophoresis of Wheat Proteins. 1. Uncoated Capillaries," *J. Agric. Food Chem* 1999 47(10):4246-55.

Beckers J.L. et al., "Sample Stacking in Capillary Zone Electrophoresis: Principles, Advantages and Limitations," *Electrophoresis* 2000 21(14):2747-2767.

Beckers J.L. et al., "System Zones in Capillary Zone Electrophoresis," *Electrophoresis* Oct. 2001; 22(17):3648-3658.

Bharadwaj R. et al., "Design and Optimization of On-Chip Capillary Electrophoresis," *Electrophoresis* 2002 23(16):2729-2744.

Bossuyt X., "Separation of Serum Proteins by Automated Capillary Zone Electrophoresis," *Clin Chem Lab Med.* 2003 41(6):762-772.

Bromberg A. et al., "Multichannel Homogeneous Immunoassay for Detection of 2,4,6-Trinitrotoluene (TNT) Using a Microfabricated Capillary Array Electrophoresis Chip," *Electrophoresis* 2004 25(12):1895-1900.

Chen G. et al., "Fast and Simple Sample Introduction for Capillary Electrophoresis Microsystems," *Analyst* 2004 129(6):507-511 (Epub Apr. 20, 2004).

Chen S.H. et al., "Flow-Through Sampling for Electrophoresis-Based Microchips and Their Applications for Protein Analysis," *Anal. Chem.* 2002 74(19):5146-5153.

Doherty E.A. et al., "Microchannel Wall Coatings for Protein Separations by Capillary and Chip Electrophoresis," *Electrophoresis* 2003 24(1-2):34-54.

Du Y. et al., "Microchip Capillary Electrophoresis with Solid-State Electrochemiluminescence Detector," *Anal. Chem.* 2005 77(24):7993-7997.

Futterer C. et al., "Injection and Flow Control System for Microchannels," *Lab Chip.* 2004 4(4):351-356 (Epub May 11, 2004).

Ganzler K. et al., "High-Performance Capillary Electrophoresis of SDS-Protein Complexes Using UV-Transparent Polymer Networks," *Anal. Chem.* 1992 64:2665-2671.

Gebauer P. et al., "Theory of System Zones in Capillary Zone Electrophoresis," *Electrophoresis* 2003 23(12):1779-1785.

Griffiths S.K. et al., "Design and Analysis of Folded Channels for Chip-Based Separations," *Anal. Chem.* 2002 74(13):2960-2967.

Hilhorst M.J. et al., "Capillary Electrokinetic Separation Techniques for Profiling of Drugs and Related Products," *Electrophoresis* 2001 22(12):2542-2564.

Hjerten S. et al., "High-Performance Electrophoresis of Acidic and Basic Low-Molecular-Weight Compounds and Proteins in the Presence of Polymers and Neutral Surfactants," *J. Liquid Chromatog.* 1989 12: 2471-2499.

Hong J.W. et al., "Microfabricated Polymer Chip for Capillary Gel Electrophoresis," *Biotechnol. Prog.* 2001 17(5):958-962.

Jung B. et al., "On-Chip Millionfold Sample Stacking Using Transient Isotachophoresis," *Anal. Chem.* 2006 78(7):2319-2327.

Kasicka V., "Recent Advances in Capillary Electrophoresis and Capillary Electrochromatography of Peptides," *Electrophoresis* 2004 24(22-23):4013-4046.

Kasicka V., "Recent Advances in Capillary Electrophoresis of Peptides," Electrophoresis 2001 22(19):4139-4162.

Kemp G., "Capillary electrophoresis: a versatile family of analytical techniques," *Biotechnol. Appl. Biochem.* 1998 27:9-17.

Kremser L. et al., "Capillary Electrophoresis of Biological Particles: Viruses, Bacteria, and Eukaryotic Cells," *Electrophoresis* 2004 25(14):2282-2291.

Lausch R. et al., "Rapid Capillary Gel Electrophoresis of Proteins," *J. Chromatogr.* 1993 654:190-195.

Lee G.B. et al., "On the Surface Modification of Microchannels for Microcapillary Electrophoresis Chips," *Electrophoresis* 2005 26(24):4616-4624.

Li H.F. et al., "A Compactly Integrated Laser-Induced Fluorescence Detector for Microchip Electrophoresis," *Electrophoresis* 2004 25(12):1907-1915.

M.W. et al., "Design and Characterization of Poly(Dimethylsiloxane)-Based Valves for Interfacing Continuous-Flow Sampling to Microchip Electrophoresis," *Anal Chem.* 2006 78(4):1042-1051.

Lichtenberg J. et al., "A Microchip Electrophoresis System With Integrated In-Plane Electrodes for Contactless Conductivity Detection," *Electrophoresis* 2002 23(21):3769-3780.

Liu J. et al., "Surface-Modified Poly(Methyl Methacrylate) Capillary Electrophoresis Microchips for Protein and Peptide Analysis," *Anal. Chem.* 2004 76(23):6948-6955.

Liu Y. et al., "Stacking Due to Ionic Transport Number Mismatch During Sample Sweeping on Microchips," *Lab Chip* 2005 5(4):457-465 (Epub Mar. 7, 2005).

Manabe T. et al., "Size Separation of Sodium Dodecyl Sulfate Complexes of Human Plasma Proteins by Capillary Electrophoresis Employing Linear Polyacrylamide as a Sieving Polymer," *Electrophoresis* 1998 19:2308-2316.

Martin J. et al., "Mechanical and Acoustical Properties as a Function of PEG Concentration in Macroporous Silica Gels," *J. Non-Crystalline Solids* 2001 285:222-229.

Menzinger F. et al., "Analysis of Agrochemicals by Capillary Electrophoresis," *J Chromatogr A.* 2000 891(1):45-67.

Monton M.R., "Recent Developments in Capillary Electrophoresis-Mass Spectrometry of Proteins and Peptides," *Anal Sci.* 2005 21(1):5-13.

Pallandre A. et al., "Surface Treatment and Characterization: Perspectives to Electrophoresis and Lab-On-Chips," *Electrophoresis* 2006 27(3):584-610.

Petsev D.N. et al., "Microchannel Protein Separation by Electric Field Gradient Focusing," *Lab Chip* 2005 5(6):587-597 (Epub Apr. 15, 2005).

Quirino J.P. et al., "Sample Stacking of Cationic and Anionic Analytes in Capillary Electrophoresis," *J Chromatogr A.* 2001 902(1):119-135.

Richards P. et al., "Functional Proteomics Using Microchannel Plate Detectors," *Proteomics* 2002 2(3):256-261.

Rossier J. et al., "Polymer Microfluidic Chips for Electrochemical and Biochemical Analyses," *Electrophoresis* 2002 23(6):858-867.

Schwartz H. et al., "Separation of Proteins and Peptides by Capillary Electrophoresis: Application to Analytical Biotechnology," *Beckman BioResearch Literature* No. 727484.

Shihabi Z.K., "Stacking in Capillary Zone Electrophoresis," *J Chromatogr A.* 2000 902(1):107-117.

Wang K. et al., "Microchannel-Electrode Alignment and Separation Parameters Comparison in Microchip Capillary Electrophoresis by Scanning Electrochemical Microscopy," *J. Chromatogr.* 2006 A. 1110(1-2):222-226 (Epub Feb. 3, 2006).

Wu D. et al., "Sodium Dodecyl Sulfate-Capillary Gel Electrophoresis of Proteins Using Non-Cross-Linked Polyacrylamide," *J. Chromatogr.* 1992 608:349-356.

Xuan X. et al., "Accelerated Particle Electrophoretic Motion and Separation in Converging-Diverging Microchannels," *Anal. Chem.* 2005 77(14):4323-4328.

English Translation of Chinese Office Action for Chinese Patent Application No. 200680030934.3, dated Nov. 9, 2010, 12 pages.

English Translation of Japanese Office Action for Japanese Patent Application No. 2008-518217, dated Sep. 13, 2011, 3 pages.

English Translation of Second Chinese Office Action for Chinese Patent Application No. 200680030934.3, dated Nov. 8, 2011, 4 pages.

Sol-Gel Concentrator
Concentration Region

Separation Region

Detection Window

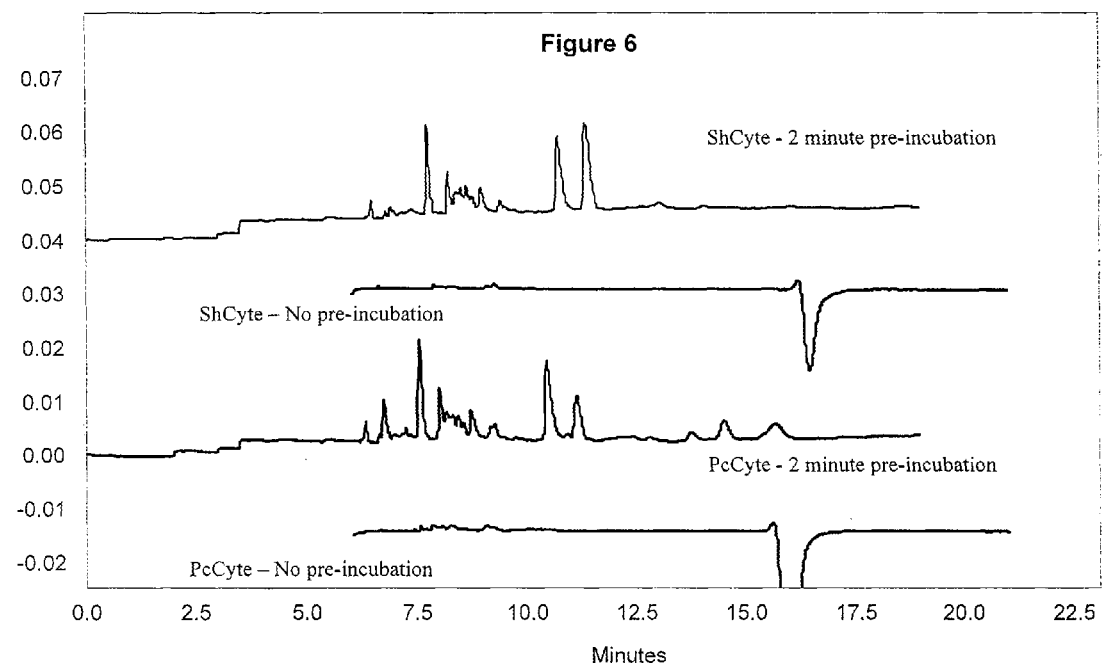

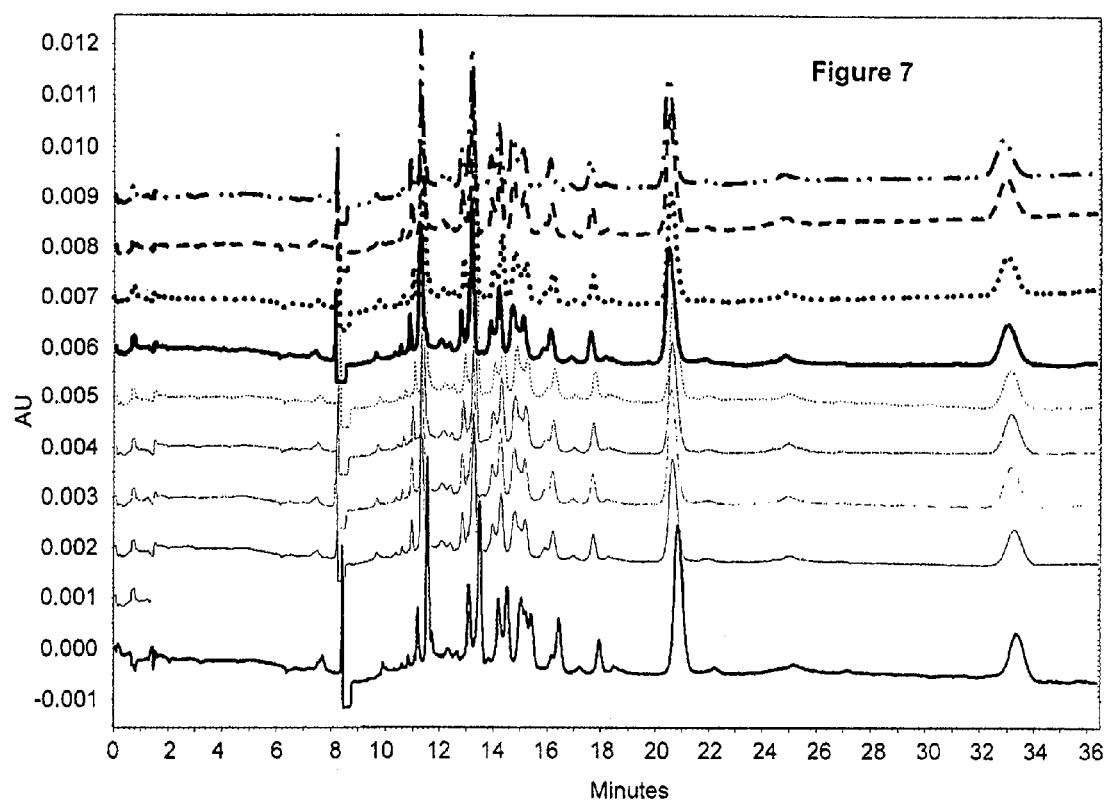

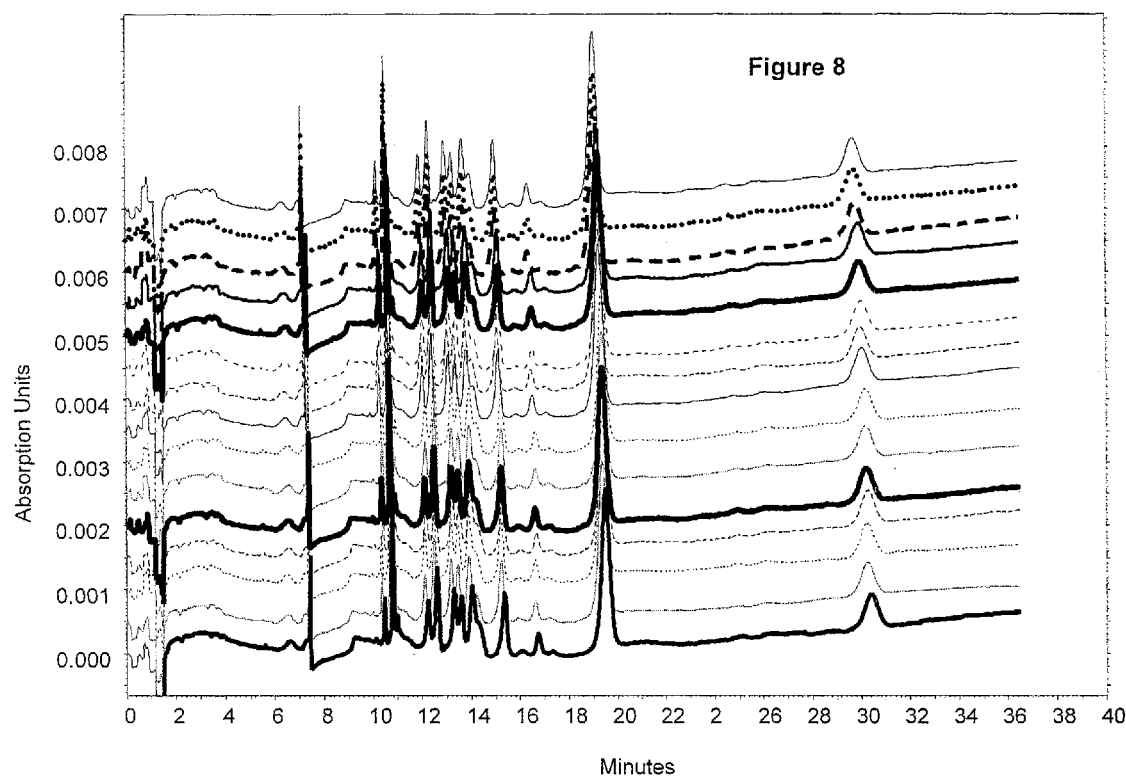

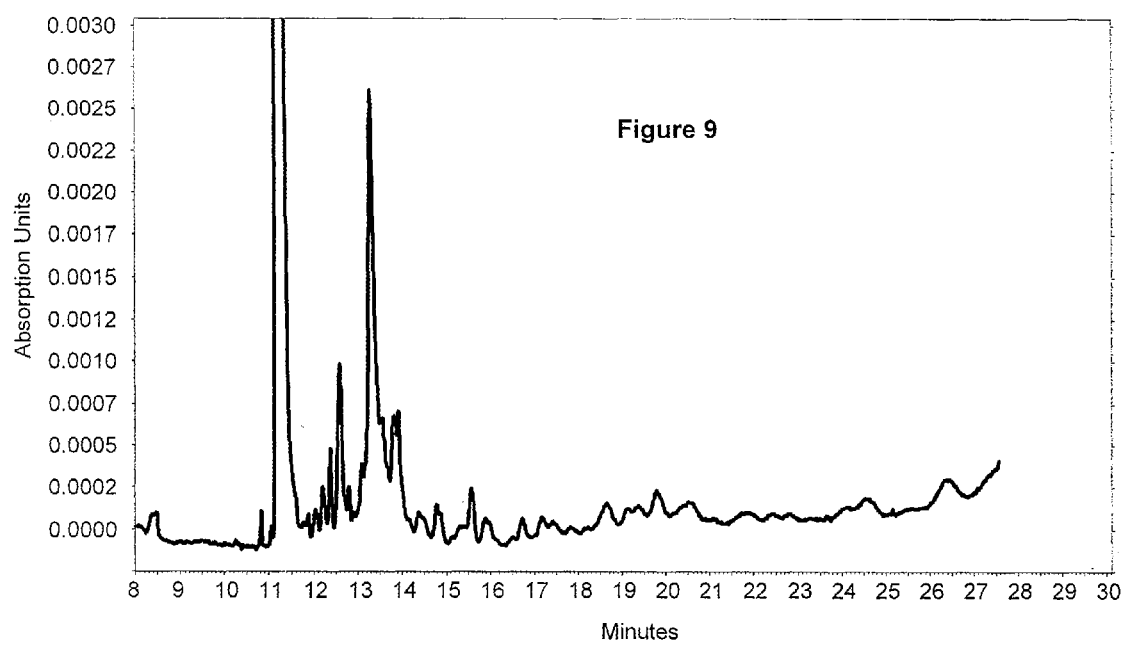

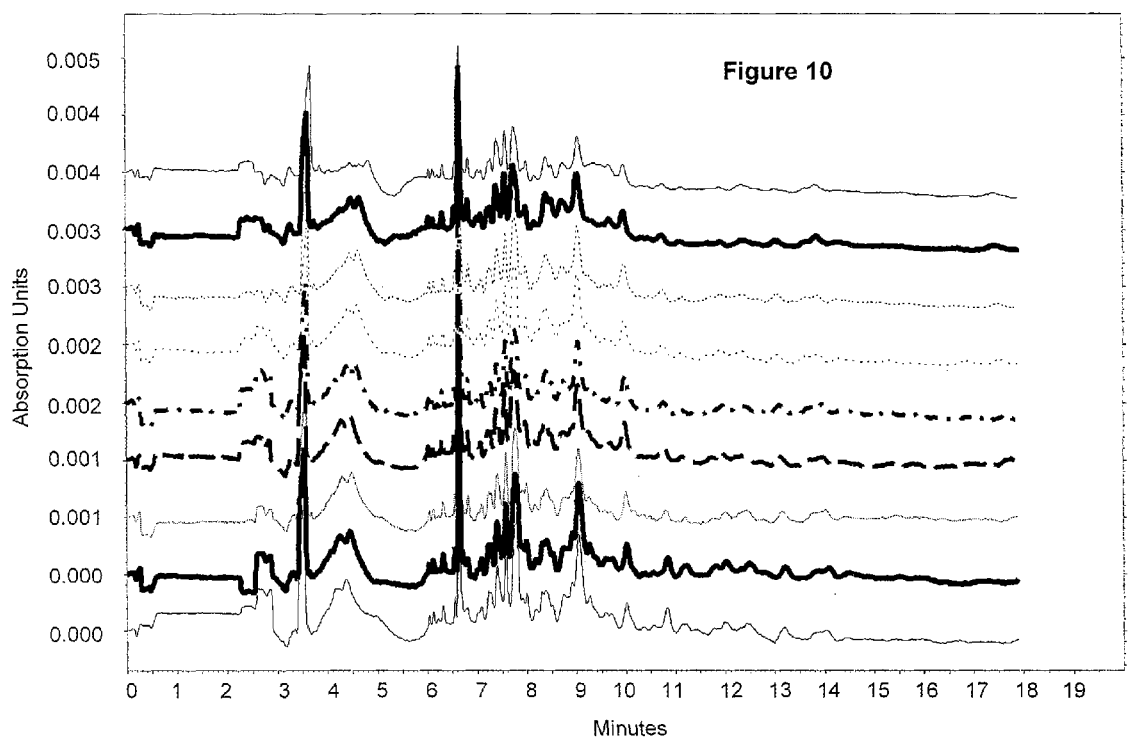

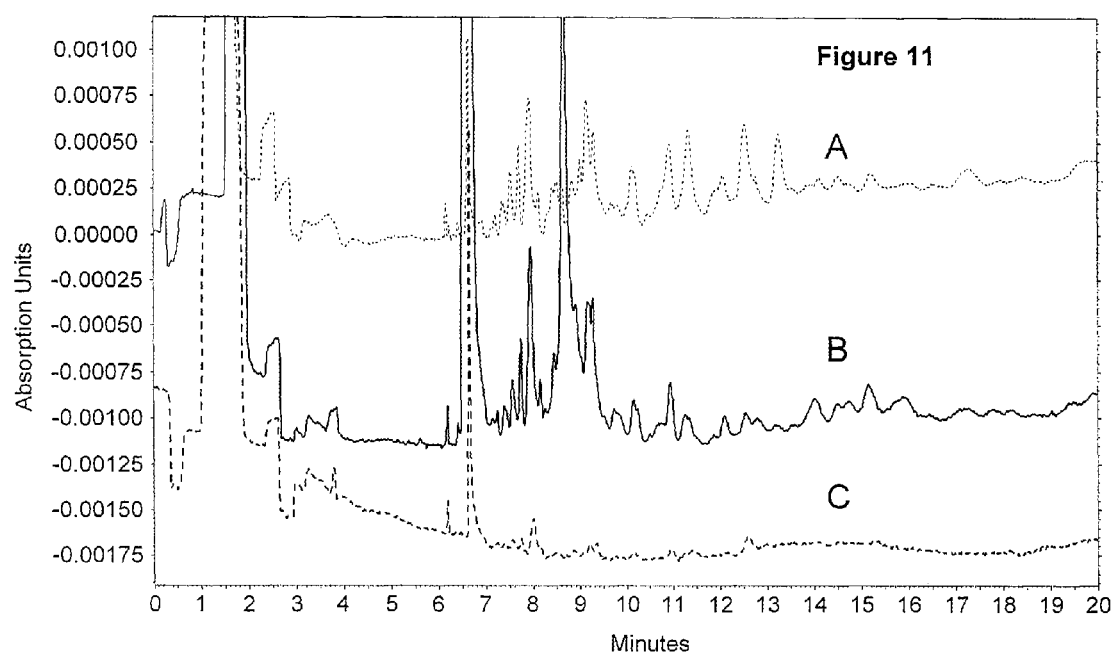

METHOD FOR FORMING A CONCENTRATING DEVICE

CROSS-REFERENCE TO RELATED APPLICATIONS

This application is a continuation of U.S. patent application No. Ser. 11/446,130, filed Jun. 5, 2006, now abandoned which claims priority from U.S. Patent Application No. 60/693,047, filed on Jun. 23, 2005, which are herein incorporated by reference in their entirety for all purposes.

FIELD OF THE INVENTION

The present invention relates to novel methods and apparatus for improving the sensitivity of capillary zone electrophoresis (CZE). The invention particularly concerns devices comprising a channel that contains an in-line sol-gel column to concentrate samples being subjected to capillary zone electrophoresis, and the use of such devices to enhance the sensitivity of capillary zone electrophoresis.

BACKGROUND OF THE INVENTION

There is a growing need for analysis of biomolecules, including proteins, polypeptides and DNA. Capillary electrophoresis (CE) is a process for separating molecules based on their size or charge. In capillary electrophoresis molecules are introduced into a fluid-filled capillary tube and subjected to an electric field (see, Kemp, G. (1998) "CAPILLARY ELECTROPHORESIS: A VERSATILE FAMILY OF ANALYTICAL TECHNIQUES," Biotechnol. Appl. Biochem. 27:9-17; Wu, D. et al. (1992). Capillary electrophoresis techniques are reviewed by Schwartz, H. et al. ("SEPARATION OF PROTEINS AND PEPTIDES BY CAPILLARY ELECTROPHORESIS: APPLICATION TO ANALYTICAL BIOTECHNOLOGY," Beckman BioResearch Literature No. 727484).

Capillary electrophoresis (CE) has become an attractive alternative to traditional slab gel electrophoresis for biomolecular separations due to its ability to provide fast, highly efficient sample separations with minimal sample volume requirements (Monton, M. R. (2005) "RECENT DEVELOPMENTS IN CAPILLARY ELECTROPHORESIS-MASS SPECTROMETRY OF PROTEINS AND PEPTIDES," Anal Sci. 21(1):5-13). Numerous approaches for accomplishing capillary electrophoresis have been previously described (see, for example, U.S. Pat. Nos.: RE37,606; 6,440,284; 6,436,646; 6,410,668; 6,372,353; 6,358,385; 6,355,709; 6,316,201; 6,306,273; 6,274,089; 6,235,175; 6,153,073; 6,129,826; 6,107,044; 6,074,542; 6,068,752; 6,042,710; 6,033,546; 6,001,232; 5,989,399; 5,976,336; 5,964,995; 5,958,694; 5,948,227; 5,916,426; 5,891,313; 5,846,395; 5,840,388; 5,777,096; 5,741,411; 5,728,282; 5,695,626; 5,665,216; 5,582,705; 5,580,016; 5,567,292; 5,552,028; 5,545,302; 5,534,123; 5,514,543; 5,503,722; 5,423,966; 5,421,980; 5,384,024; 5,374,527; 5,370,777; 5,364,520; 5,332,481; 5,310,462; 5,292,416; 5,292,372; 5,264,101; 5,259,939; 5,139,630; 5,120,413; 5,112,460; 5,015,350; 4,865,706). Two primary separation mechanisms are commonly used in CE: procedures in which separations are obtained based on differences in the molecular size of analytes, and procedures in which separation is achieved by exploiting differences in the charge density (charge/mass ratio) of analytes.

"Capillary Gel Electrophoresis" ("CGE") is used to separate analytes based on differences in their molecular size. Typically, CGE is carried out using gel matrices of controlled pore sizes. Separations result from differences in the abilities of different sized molecule to penetrate the gel matrix. Size separation is achieved because small molecules move more rapidly through the separation gel than large molecules. In order to employ CGE with polypeptides and proteins, it is generally necessary to denature the molecules (for example, with sodium dodecyl sulfate (SDS)), so that all of the analytes will have the same effective charge density. CGE is discussed in Bean, S. R. et al. (1999) ("SODIUM DODECYL SULFATE CAPILLARY ELECTROPHORESIS OF WHEAT PROTEINS. I. UNCOATED CAPILLARIES," J. Agric. Food Chem 47(10):4246-55); Wu, D. et al. (1992) ("SODIUM DODECYL SULFATE-CAPILLARY GEL ELECTROPHORESIS OF PROTEINS USING NON-CROSS-LINKED POLYACRYLAMIDE," J. Chromatogr. 608:349-356); Lausch, R. et al. (1993) ("RAPID CAPILLARY GEL ELECTROPHORESIS OF PROTEINS," J. Chromatogr. 654:190-195); Manabe, T. et al. (1998) ("SIZE SEPARATION OF SODIUM DODECYL SULFATE COMPLEXES OF HUMAN PLASMA PROTEINS BY CAPILLARY ELECTROPHORESIS EMPLOYING LINEAR POLYACRYLAMIDE AS A SIEVING POLYMER." Electrophoresis 19:2308-2316); and Ganzier, K. et al. (1992) ("High-Performance Capillary Electrophoresis of SDS-Protein Complexes Using UV-Transparent Polymer Networks," Anal. Chem. 64:2665-2671).

In contrast, "Capillary Zone Electrophoresis" ("CZE," also known as free-solution CE (FSCE)) separates analytes based on differences in their charge densities. These differences cause differing electrophoretic mobilities, and hence differing velocities of migration. In general terms, CZE involves introducing a sample into a capillary tube and applying an electric field to the tube. The electric field pulls the sample through the tube and separates it into its constituent parts (i.e., each of the sample constituents has its own electrophoretic mobility; those having greater mobility travel through the capillary faster than those with slower mobility). As a result, the constituents of the sample are resolved into discrete zones in the capillary tube during their migration through the tube. An on-line detector can be used to continuously monitor the separation and provide data as to the various constituents based upon the discrete zones. The detector measures the absorbance of light by each constituent at a specified wavelength; different constituents absorb light differently, and, because of this, the constituents can be differentiated from each other.

Two general categories of CZE can be described, depending upon the contents of the capillary columns. In "gel" CZE, the capillary tube is filled with a suitable gel, e.g., polyacrylamide gel. Separation of the constituents in the sample is predicated in part by the size and charge of the constituents traveling through the gel matrix. In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (the buffer solution and the sample being analyzed), must also flow in this direction to maintain electroneutrality. This electroendosmatic flow provides a fixed velocity component which drives both neutral species and ionic species, regardless of charge, towards the cathode. Fused silica is principally utilized as the material for the capillary tube because it can withstand the relatively high voltage used in CZE, and because the inner walls of a fused silica capillary ionize to create the negative charge which causes the desired electroendosomatic flow (see, e.g., WO9310258A1).

To achieve optimal separation using CZE, it is important that the employed buffer solution be homogeneous and that a constant field strength be used throughout the length of the capillary. The separation relies principally on the pH controlled dissociation of acidic groups on the solute or the protonation of basic functions on the solute. Thus, the ability of CZE to separate analytes and the degree or extent of such separation can be enhanced by altering the pH of the buffer system, or by altering its ionic strength. Typically, the pH of the buffers utilized in open CZE is chosen with reference to the isoelectric points (pI) of the constituents in the sample.

CZE is discussed by Quirino, J. P. et al. (2001) ("SAMPLE STACKING OF CATIONIC AND ANIONIC ANALYTES IN CAPILLARY ELECTROPHORESIS," J Chromatogr A. 902(1):119-135); Kasicka, V. (2004) ("RECENT ADVANCES IN CAPILLARY ELECTROPHORESIS AND CAPILLARY ELECTROCHROMATOGRAPHY OF PEPTIDES," Electrophoresis 24(22-23):4013-4046); Kasicka, V. (2001) ("RECENT ADVANCES IN CAPILLARY ELECTROPHORESIS OF PEPTIDES," Electrophoresis 22(19): 4139-4162); Bossuyt, X. (2003) ("SEPARATION OF SERUM PROTEINS BY AUTOMATED CAPILLARY ZONE ELECTROPHORESIS," Clin Chem Lab Med. 41(6):762-772); and Monton, M. R. (2005) ("RECENT DEVELOPMENTS IN CAPILLARY ELECTROPHORESIS-MASS SPECTROMETRY OF PROTEINS AND PEPTIDES," Anal Sci. 21(1):5-13), in U.S. Patent Publications Nos. 2002/0029968 (Tan et al.); 2002/0055184 (Naylor et al.); 2002/0119482 (Nelson et al.); 2003/0057092 (Chien et al.); 2003/0217923 (Harrison et al.); 2003/0224436 (Nelson et al.); U.S. Pat. No. 4,483,773 (Yang); U.S. Pat. No. 4,793,920 (Cortes et al.); U.S. Pat. No. 5,120,413 (Chen et al.); U.S. Pat. No. 5,139,630 (Chen); U.S. Pat. No. 5,145,567 (Hseih et al.); U.S. Pat. No. 5,164,055 (Dubrow); U.S. Pat. No. 5,202,006 (Chen); U.S. Pat. No. 5,264,095 (Hseih et al.); U.S. Pat. No. 5,310,462 (Chen); U.S. Pat. No. 5,340,452 (Brenner et al.); U.S. Pat. No. 5,348,658 (Fuchs et al.); U.S. Pat. No. 5,405,782 (Kohn et al.); U.S. Pat. No. 5,423,966 (Wiktorowicz); U.S. Pat. No. 5,453,382 (Novotny et al.); U.S. Pat. No. 5,571,680 (Chen); U.S. Pat. No. 5,593,559 (Wiktorowicz); U.S. Pat. No. 5,599,433 (Keo et al.); U.S. Pat. No. 5,753,094 (Alter et al.); U.S. Pat. No. 5,766,435 (Liao et al.); U.S. Pat. No. 5,770,029 (Nelson et al.); U.S. Pat. No. 5,999,681 (Grabbe et al.); U.S. Pat. No. 6,007,690 (Nelson et al.); U.S. Pat. No. 6,074,541 (Srinivasan et al.); U.S. Pat. No. 6,074,827 (Nelson et al.); U.S. Pat. No. 6,344,326 (Nelson et al.); U.S. Pat. No. 6,416,642 (Alajoki et al.); U.S. Pat. No. 6,428,666 (Singh et al.); U.S. Pat. No. 6,432,290 (Harrison et al.); U.S. Pat. No. 6,475,362 (Gorfinkel et al.); U.S. Pat. No. 6,475,363 (Ramsey); U.S. Pat. No. 6,613,525 (Nelson et al.); U.S. Pat. No. 6,664,104 (Pourahmadi et al.); U.S. Pat. No. 6,686,035 (Jiang et al.); U.S. Pat. No. 6,695,009 (Chien et al.); U.S. Pat. No. 6,759,126 (Malik et al.); U.S. Pat. No. 6,764,817 (Schneider); U.S. Pat. No. 6,770,201 (Shepodd et al.); and U.S. Pat. No. 6,787,016 (Tan et al.); in European Patent Documents No. EP 0852007A1; EP 0572604A1; EP0518475A1; and EP0517370A1; and in PCT Publication No. WO9310258A1.

The high peak capacity (i.e., the number of peaks separated per unit time) of CZE makes it a desirable approach to the analysis of a wide range of biomolecules, including proteins and peptides (Kasicka, V. (2004) "RECENT ADVANCES IN CAPILLARY ELECTROPHORESIS AND CAPILLARY ELECTROCHROMATOGRAPHY OF PEPTIDES," Electrophoresis 24(22-23):4013-4046; Kasicka, V. (2001) "RECENT ADVANCES IN CAPILLARY ELECTROPHORESIS OF PEPTIDES," Electrophoresis 22(19):4139-4162; Bossuyt, X. (2003) "SEPARATION OF SERUM PROTEINS BY AUTOMATED CAPILLARY ZONE ELECTROPHORESIS," Clin Chem Lab Med. 41(6):762-772; Monton, M. R. (2005) "RECENT DEVELOPMENTS IN CAPILLARY ELECTROPHORESIS-MASS SPECTROMETRY OF PROTEINS AND PEPTIDES," Anal Sci. 21(1):5-13); nucleic acid molecules (Mitchelson, K. R. (2001) "THE APPLICATION OF CAPILLARY ELECTROPHORESIS FOR DNA POLYMORPHISM ANALYSIS," Methods Mol Biol. 162:3-26); drugs (Hilhorst, M. J. et al. (2001) "CAPILLARY ELECTROKINETIC SEPARATION TECHNIQUES FOR PROFILING OF DRUGS AND RELATED PRODUCTS," Electrophoresis 22(12):2542-2564), agricultural compounds (Menzinger, F. et al. (2000) "ANALYSIS OF AGROCHEMICALS BY CAPILLARY ELECTROPHORESIS," J Chromatogr A. 891(1):45-67), and even bacteria and viruses (Kremser, L. et al. (2004) "CAPILLARY ELECTROPHORESIS OF BIOLOGICAL PARTICLES: VIRUSES, BACTERIA, AND EUKARYOTIC CELLS," Electrophoresis 25(14):2282-2291).

Although CZE has multiple advantages, the CZE detection limit based on concentrations is far less than that of HPLC, and is not sufficient for many practical applications. The limitations of CZE reflect the very short in-capillary path length (i.e., detector window) of the flow cell of capillary tubes (typically only 1% of the path length of an HPLC flow cell). The short path length means that higher concentrations of analytes must be present in order to be detected (Shihabi, Z. K. (2000) "STACKING IN CAPILLARY ZONE ELECTROPHORESIS," J Chromatogr A. 902(1):107-117)

In certain situations, the concentrations of analytes found in a sample may therefore be too low to permit the use of CZE separation methods. Although such samples may be concentrated using conventional methods, the resulting small volumes encumber sample manipulation, and such handling may cause a loss of analyte. In some cases the ionic profile of samples may be compromised by electrokinetic injection, leading to poor accuracy. High salt content in the sample may also lead to problems with high localized currents causing unwanted heating.

One approach to the problem of improving the sensitivity of CZE involves adjusting the capillary detection window (Quirino, J. P. et al. (2001) "SAMPLE STACKING OF CATIONIC AND ANIONIC ANALYTES IN CAPILLARY ELECTROPHORESIS," J Chromatogr A. 902(1):119-135). Such adjustments can provide a ten-fold improvement in response. Enhanced detection means have also been employed to address the problem of analyzing dilute samples. Such means have included mass spectrometry, optical fluorescence, electrochemical oxidation or reduction, plasma resonance, radioactivity, refractive index, and conductivity. Very dilute analytes can remain undetectable despite the use of the most sensitive of known detection methods (see, e.g., Naylor et al. (U.S. Pat. No. 5,800,692)).

Another way to improve detection of dilute analytes is to concentrate the analytes prior to, or concurrent with, separation. Preseparation or concurrent analyte concentration methods, coupled with the use of a sensitive detection method, greatly increase the usefulness and efficacy of CE. Present off-line preseparation concentration methods are, however, time-consuming and suffer from various sample-handling risks such as contamination or sample loss due to spill or adsorption onto container walls. Various on-line focusing methods have been developed in response to these problems. One approach to the problem involves manipulating the composition of the sample and background solutions to cause the analyte molecules to "stack." Stacking is obtained when ionized analyte molecules, placed in a low conductivity region of the column are induced by an electric field to move to a high conductivity region of the column. Because the low conductivity region will experience a higher electric field than the high conductivity region, analyte molecules in the low conductivity region will migrate rapidly to the barrier between the two regions, thereby causing a 10- to more than 1,000-fold enhancement in the sensitivity of detection (Quirino, J. P. et al. (2001) "SAMPLE STACKING OF CATIONIC AND ANIONIC ANALYTES IN CAPILLARY ELECTROPHORESIS," J Chromatogr A. 902(1): 119-135; Shihabi, Z. K. (2000) "STACKING IN CAPILLARY ZONE ELECTROPHORESIS," J Chromatogr A. 902(1):107-117; Gebauer, P. et al. (2003) "THEORY OF SYSTEM ZONES IN CAPILLARY ZONE ELECTROPHORESIS," Electrophoresis 23(12):1779-1785; Beckers, J. L. et al. (2000) "SAMPLE STACKING IN CAPILLARY ZONE ELECTROPHORESIS: PRINCIPLES, ADVANTAGES AND LIMITATIONS," Electrophoresis 21(14):2747-2767; Beckers, J. L. et al. (2001) "SYSTEM ZONES IN CAPILLARY ZONE ELECTROPHORESIS," Electrophoresis Oct; 22(17):3648-3658).

While such stacking is thus of some benefit, it has certain significant limitations. Significantly, although stacking improves the ability to detect an analyte, it also increases the concentration of contaminating analyte species. Stacking is possible only in situations in which the target analyte is present at a concentration below that of the background electrolytes (Beckers, J. L. et al. (2000) "SAMPLE STACKING IN CAPILLARY ZONE ELECTROPHORESIS: PRINCIPLES, ADVANTAGES AND LIMITATIONS," Electrophoresis 21(14):2747-2767). Moreover, the ability to resolve two analytes in CZE is directly proportional to one-half the difference in their respective migration times, and inversely proportional to the sum of the standard deviations of the analyte peaks. Thus, since the size of the analyte peaks is affected by the sample volume, the use of larger sample volumes can adversely affect peak resolution (Beckers, J. L. et al. (2000) "SAMPLE STACKING IN CAPILLARY ZONE ELECTROPHORESIS: PRINCIPLES, ADVANTAGES AND LIMITATIONS," Electrophoresis 21(14):2747-2767). Methods of accomplishing stacking are discussed by Shihabi, Z. K. (2000) ("STACKING IN CAPILLARY ZONE ELECTROPHORESIS," J Chromatogr A. 902(1):107-117). The art has therefore sought alternative solutions to enhance the sensitivity of CZE.

Various mechanical measures have been used to facilitate the concentration of analytes. Guzman (U.S. Pat. No. 5,202,010) discloses an analyte concentrator comprising a tubular structure containing fluid-permeable end plates and a plurality of small bodies coated with antibodies or other chemical entities selected for their ability to bind to target analytes in the sample being analyzed. In operation, after being permitted to contact the sample analytes, the capillary is washed to remove excess material, and the trapped target analytes, which have been concentrated onto the small bodies of the structure, are then removed and processed for study. As will be appreciated, significant handling of the analytes is required. Guzman (U.S. Pat. No. 6,406,604) discloses an analyte concentrator having greater efficiency. The disclosed apparatus comprises a relatively large-bore transport capillary that intersects with a plurality of small-bore separation capillaries. Analyte present in the large bore capillary become captured and accumulate at the sites of intersection between the large-bore capillary and the separation capillaries. Naylor et al. (U.S. Pat. No. 5,800,692) describe a preseparation processor for use in capillary electrophoresis. The processor contains a sample processing material, preferably in the form of a membrane, gel or packed beads, for concentrating or chemically processing a sample, or catalyzing a chemical reaction. It is stated to be particularly suited to the concentration of dilute samples or the purification of contaminated samples. Zare et al. (U.S. Pat. No. 6,136,187) disclose a frit-less capillary separation device in which particles are embedded in a porous silane sol-gel matrix. Charged and uncharged molecules are embedded into the sol-gel matrix. The volatile components are allowed to evaporate, producing a hard porous glass. Different functionalized or derivatized sol-gel precursors can be used to prepare sol-gel glasses with different physical properties, such as pore size and surface charge. The porosity of the glass allows diffusion of protons and other neutral or ionic species, but restricts significant amounts of chromatographic particles from leaving the glass matrix. While the approach of Zare et al. (U.S. Pat. No. 6,136,187) provides certain advantages, considerable time is required to prepare the columns, and the requirement that the matrix be inoculated with sample prior to solidification limits peak resolution.

Thus, despite all such prior advances, a need remains for methods and apparatus that could overcome the problems of analyzing dilute samples and thereby extend the utility of CZE to permit the analysis of low concentration samples. The present invention is directed to this and other needs.

SUMMARY OF THE INVENTION

In detail, the invention provides a sol-gel concentrating device comprising a channel that contains a column of a monolith of a polymerized alkylsilicate gel matrix containing chromatographic sorbent particles, wherein the gel matrix is polymerized under conditions sufficient to permit evaporation of solvent without substantial destabilization of the monolith.

The invention particularly concerns the embodiment of such sol-gel concentrating device wherein the channel is a microchannel, a capillary tube, a column, etc. The invention particularly concerns the embodiments of such a device wherein the gel matrix is polymerized within a capillary tube that is bounded by porous frits, and a micro-channel embedded within a chip or plate.

The invention additionally concerns the embodiments of such sol-gel concentrating devices wherein the alkylsilicate gel matrix is a tetraethylorthosilicate gel matrix, wherein the chromatographic sorbent particles are octadecylsilica particles, and/or wherein the sol-gel is polymerized via stepwise, multistep incubation.

The invention particularly concerns the embodiments of such sol-gel concentrating devices wherein the step-wise, multistep incubation comprises heating under conditions suitable to promote the polymerization of the monolith without causing significant evaporation of solvent, followed by incubation under conditions sufficient to promote the evaporation of solvent from the polymerized monolith, followed by incubation under conditions sufficient to cure the alkylsilicate gel matrix. The invention particularly concerns the embodiments of such sol-gel concentrating devices wherein the device is employed in an analytical or preparative process to promote the concentrating of an analyte of a sample.

The invention additionally concerns the embodiments of such sol-gel concentrating devices wherein the analytical or preparative process is selected from the group consisting of liquid chromatography, capillary zone electrophoresis, capillary electrophoresis, capillary electrochromatography (CEC), reverse phase chromatography, ion-exchange chromatography, affinity chromatography and normal phase chromatography.

The invention particularly concerns the embodiments of such sol-gel concentrating devices wherein the analytical or preparative process is selected from the group consisting of an immunoassay and an enzymatic reaction, and/or wherein the analyte is selected from the group consisting of: a protein, a peptide, a nucleic acid molecule, a drug, an agricultural compound, a bacteria and a virus.

The invention further provides a method for concentrating an analyte in a sample being subjected to an analytical or preparative process, wherein the method comprises concentrating the analyte using a sol-gel concentrating device comprising a monolith of a polymerized alkylsilicate gel matrix containing chromatographic sorbent particles, wherein the gel matrix is polymerized under conditions sufficient to permit evaporation of solvent without substantial destabilization of the monolith.

The invention particularly concerns the embodiments of such method wherein the device is polymerized within a capillary tube, and is bounded by porous frits, wherein the alkylsilicate gel matrix is a tetraethylorthosilicate gel matrix, wherein the chromatographic sorbent particles are octadecylsilica particles, and/or wherein the sol-gel is polymerized via step-wise, multistep incubation.

The invention additionally concerns the embodiments of such methods wherein the step-wise, multistep incubation comprises heating under conditions suitable to promote the polymerization of the monolith without causing significant evaporation of solvent, followed by incubation under conditions sufficient to promote the evaporation of solvent from the polymerized monolith, followed by incubation under conditions sufficient to cure the alkylsilicate gel matrix.

The invention particularly concerns the embodiments of such methods wherein the device is employed in an analytical or preparative process to promote the concentrating of an analyte of a sample.

The invention additionally concerns the embodiments of such methods wherein the analytical or preparative process is selected from the group consisting of liquid chromatography, capillary zone electrophoresis, capillary electrophoresis, capillary electrochromatography (CEC), reverse phase chromatography, ion-exchange chromatography, affinity chromatography and normal phase chromatography.

The invention particularly concerns the embodiments of such methods wherein the analytical or preparative process is selected from the group consisting of an immunoassay and an enzymatic reaction.

The invention additionally concerns the embodiments of such methods wherein the analyte is selected from the group consisting of: a protein, a peptide, a nucleic acid molecule, a drug, an agricultural compound, a bacteria and a virus.

BRIEF DESCRIPTION OF THE FIGURES

FIG. 6 shows the ability of the concentrating devices of the present invention to separate digest products of sheep cytochrome C (ShCytc) and pig cytochrome C (PcCytc), consisting of identical amino acid sequences).

FIG. 7 shows the reproducibility of analyte separation using the concentrating devices of the present invention. Shown are the separation profiles for runs 1-10 of samples containing reduced and alkylated Hcytc, after 15 runs on another instrument.

FIG. 8 shows the reproducibility of analyses of digests of Hcytc.

FIG. 9 shows the ability of the methods and apparatus of the present invention to separate peptide digestion products of yeast hexokinase.

FIG. 10 shows the reproducibility of multiple analyses of digests of yeast hexokinase.

FIG. 11 illustrates the ability of the devices of the present invention to detect extremely low amounts of analytes. The traces show electroferograms of bovine hexokinase digests obtained using a sol-gel capillary for different time intervals: 0.2 picomoles (pmoles) injected and 1.0 pmoles/µl eluted (Trace A); 6.25 pmoles injected and 89 fmoles/µl eluted (Trace B); 1.25 fmoles injected and 17.8 fmoles/µl eluted (Trace C).

DESCRIPTION OF THE PREFERRED EMBODIMENTS

The present invention relates to novel methods and apparatus for improving the sensitivity of analytical or preparative techniques (such as capillary zone electrophoresis (CZE), etc.) and, in particular, addresses the need to extend the utility of such techniques to permit their use in the analysis of analytes present in a sample at low concentration. The invention particularly concerns concentrating devices that comprise channels containing in-line sol-gel columns.

As used herein, the term "channel" is intended to broadly encompass a device that permits the flow of analytes. Such channels, and the columns within them may be of any length or geometry (e.g., cylindrical, "V"-shaped, open troughs, closed tubular, etc.). The devices may comprise a porous column packing material bounded by porous frits. Suitable channels may be preparative or analytical columns (e.g., channels having an internal cross-sectional diameter of >2 mm), capillaries (e.g., channels having an internal cross-sectional diameter of 20 µm-2 mm), or microchannels (e.g., channels having an internal cross-sectional diameter of <20 µm), etc.

As used herein, the term "gel" is intended to refer to a system of at least two components, in which one component provides a sufficient structural framework for rigidity and other component(s) fill(s) the space between the structural units or spaces (see, The Encyclopedia of Chemistry, 4$^{th}$ Edition (Considine et al., Van Nostrum Reinhold, New York (1984), page 272). The term "gel" is often used to refer only to cross-linked polymers, rather than linear or branched polymers (such as dextrans) involving entangled monomers (see, e.g., Hjerten, S. et al. (1989) "HIGH-PERFORMANCE ELECTROPHORESIS OF ACIDIC AND BASIC LOW-MOLECULAR-WEIGHT COMPOUNDS AND PROTEINS IN THE PRESENCE OF POLYMERS AND NEUTRAL SURFACTANTS," J. LIQUID CHROMATOG. 12: 2471-2499), however, non-crosslinked dextran and polyacrylamide matrices used in capillary electrophoresis have nevertheless also been considered to be "gels (see, e.g., Kemp, G. (1998) "CAPILLARY ELECTROPHORESIS: A VERSATILE FAMILY OF ANALYTICAL TECHNIQUES," Biotechnol. Appl. Biochem. 27:9-17; Wu, D. et al. (1992) ("SODIUM DODECYL SULFATE-CAPILLARY GEL ELECTROPHORESIS OF PROTEINS USING NON-CROSS-LINKED POLYACRYLAMIDE," J. Chromatogr. 608:349-356). The gels of the present invention may be composed of either cross-linked or non-crosslinked polymers.

Figure 1:
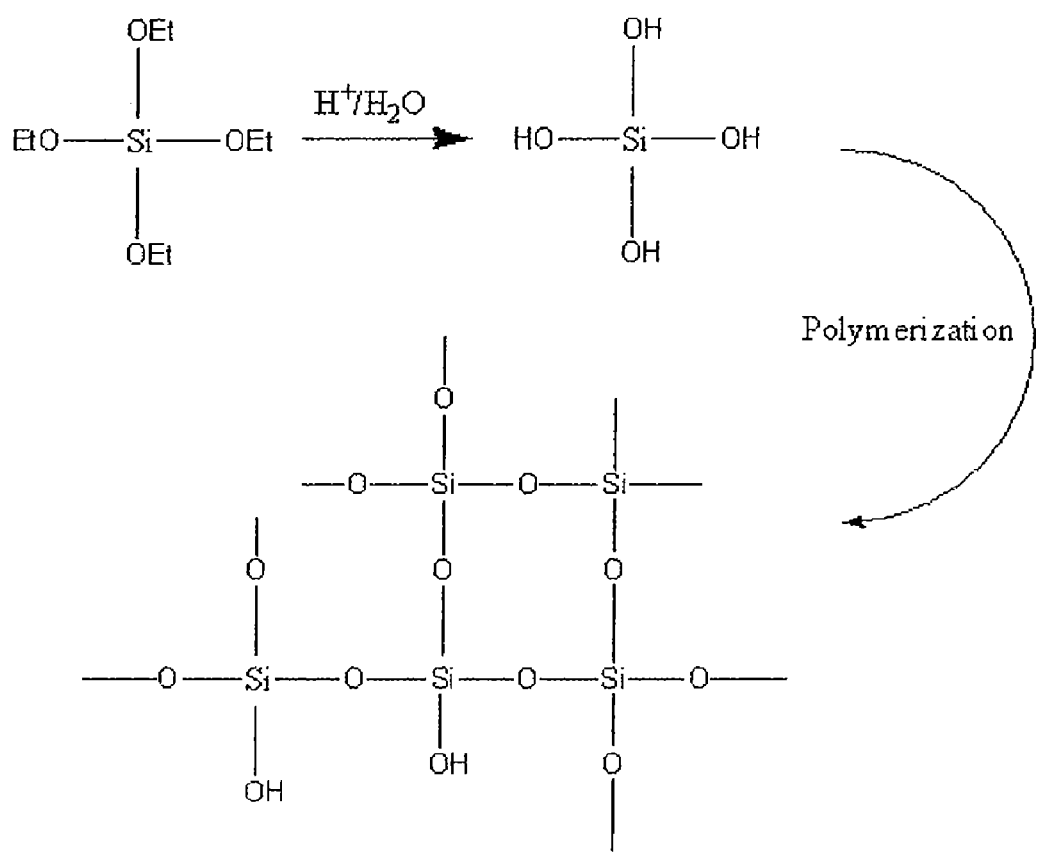
FIG. 1 illustrates the hydrolysis and polymerization of TEOS in accordance with a preferred embodiment of the present invention.

The term "sol-gel" as used herein denotes an inorganic, catalytic silicon oxide gel, comprising small particles ("sols") suspended within a polymerized matrix ("gel"). The sol-gel of the concentrating device(s) of the present invention will preferably comprise a silica sol-gel plug, especially a sol-gel plug that has been thermally polymerized to form a single continuous polymerized matrix ("monolith"). In a preferred embodiment, this invention employs a metal alkoxide sol-gel process. The metal alkoxide sol-gel process is a method of preparing metal oxide glasses by hydrolyzing a solution of water, alcohol, and a metal alkoxide source. The sources of these metal oxides, or silanes, are the alkoxy compounds of type $R_nSi(OR')_{4-n}$ as described by C. J. Brinker et al. in Sol-Gel Science, Academic Press, Inc., New York, N.Y., 1990. The most commonly used of these compounds is tetraethylorthosilicate $(Si(OC_2H_5)_4)$ ("TEOS"), although other compounds such as titanates, and zirconates may also be used. FIG. 1 illustrates the hydrolysis and polymerization of TEOS in accordance with a preferred embodiment of the present invention. As these substances polymerize, gelation of the solution occurs. If the volatile solvents in the wet gel are allowed to evaporate, the gel shrinks and hardens, creating a hard porous glass. Most preferably, such plugs can be produced by introducing a mixture comprising: (a) an alkyl siloxane having three alkoxy groups and a alkyl chain or bis (trialkoxysilyl) compounds, etc., such as an alkylsilicate (e.g., tetraethylorthosilicate), (b) an organic solvent (e.g., ethanol, methanol, propanol, toluene, etc.), and (c) an inorganic acid (e.g., hydrochloric acid, phosphoric acid, nitric acid, etc. (the use of nitric acid is preferred) into the capillary tube, and then heating the mixture until a gel forms.

In preferred embodiments, sol of the sol-gel column will comprise a particle, for example, polystyrene, latex, ion-exchange resin, polyacrylamide, nylon, polyvinylpyrrolidone, or octadecylsilica (ODS) particles such as Ultrasphere particles (Beckman Coulter, Inc.). Such particles can be of any of a variety of desired sizes and will preferably be porous, possessing any of a variety of desired pore sizes which shall depend on the size of the analytes that are to be separated (e.g., 100 Å, 500 Å, 3 µm, 5 µm, 10 µm, etc.). The particles are preferably coated with a silane, especially a silane having 4, 8, or 18 carbons). The surface(s) of the particles are preferably modified with organic or inorganic functional groups. Organic polymers (such as polyethylene glycol) may additionally be included. The pore sizes of the gel can be controlled by varying the size of the sorbent particles or the ratios of water and organic solvent employed (Martin, J. et al. (2001) "MECHANICAL AND ACOUSTICAL PROPERTIES AS A FUNCTION OF PEG CONCENTRATION IN MACROPOROUS SILICA GELS," J. Non-Crystalline Solids 285:222-229).

Any of a wide range of compositions may be used in the sol-gel columns of the concentrating devices of the present invention. For example, the use of nitric acid in the range of 0.1 M to 1.0 M is acceptable. As a further example, a suitable composition may comprise TEOS (e.g., 356 µl of 99.9% TEOS) without the addition of an organic solvent. The use of different relative concentrations of the components of such compositions will alter the properties of the resulting solgel monolith such as porosity and mechanical strength. An exemplary composition contains approximately 200 µl of 99.9% TEOS dissolved in approximately 156 µl of 99.5% ethanol and mixed with approximately 258 µmoles of nitric acid (e.g., 258 µl of 1.0 N $HNO_3$). Approximately 485 mg of particles (forming a 75% w/v composition) is employed with such gel components. Such compositions can be scaled up or down to accommodate desired sol-gel volumes.

The sol-gel column of the devices of the present invention is preferably polymerized using heat, and most preferably, a step-wise, multistep heating process will be employed. In one preferred multi-step process, the sol-gel components are heated under conditions suitable to accelerate the polymerization of the gel materials without causing significant evaporation of the ethanol. In such heating step, evaporation is considered "significant" if it is of an extent sufficient to cause substantial destabilization of the monolith. Incubations at temperatures of between 35°-60° C. are suitable. More preferably, a two-step process is employed in which the temperature is initially about 35°-45° C., and is then raised to about 45°-55° C. An exemplary two-step procedure involves heating the sol-gel for approximately 18 hours at about 40° C. followed by an approximately 1 hour incubation at about 50° C.

Following such treatment, the sol-gel materials are preferably subjected to further heating at temperatures sufficient to promote ethanol evaporation (e.g., 60°-80° C.). An exemplary procedure involves heating the sol-gel for approximately 16-18 hours at about 70° C. As the formation of the polymer network ("matrix") has already been initiated, the evaporation of the ethanol does not substantially destabilize the monolith. As used herein, a monolith of the present invention is said to have been "substantially" destabilized if it exhibits cracks, fissures or other defects that preclude its use as a concentrating device in accordance with the objectives of the present invention.

Thus, the use of the multi-step incubation procedure, by delaying the evaporation of ethanol until after a polymer network has commenced to form, results in a polymer network that is sufficiently strong to hold the monolith together during the ethanol evaporation. Therefore, monoliths of precise length can be made in a very reproducible manner. The prior art (Zare et al; U.S. Pat. No. 6,136,187) use of a single 100° C. heating step creates high ethanol vapor pressure prior to the formation of a strong matrix, thus destabilizing the monolith, and breaking it into small pieces.

Following such treatment, the sol-gel materials are preferably subjected to further heating at temperatures sufficient to cure the alkylsilicate gel matrix. Incubations at temperatures of between 90°-130° C. are suitable. More preferably, a two-step process is employed in which the temperature is initially about 90°-110° C., and then is raised to about 110°-130° C. An exemplary two-step procedure involves heating the sol-gel for at least approximately 1 hour at about 100° C. followed by an approximately 2 hour incubation at about 120° C. Longer incubation periods are acceptable.

In a preferred multi-step process, the sol-gel components are heated for 1 hour at 25° C., then for 16-18 hours at 40° C., then for 1 hour at 50° C. then for 16-18 hours at 70° C., then for 1 hour at 100° C., then for 2 hours at 120° C.

Polymerization is most preferably conducted wholly or partially within the channel (e.g., capillary, microchannel, etc.) desired for the device. Thus, the unpolymerized material, partially polymerized material, or completely polymerized material of the column is introduced or otherwise applied to the device to form the desired channel. The column of the resultant channel is preferably washed and equilibrated prior to use. Samples may be applied or injected into the column and concentrated onto the column by pressure, vacuum from the outlet, electrokinetically, etc. Impurities including salts, which are detrimental to MS analyzers, can be washed out prior to the elution of the sample. Sample analytes may then be eluted with a buffer containing, for example, an organic solvent able to remove some, and preferably, essentially all, of the absorbed analytes in a thin, concentrated sample plug. Application of separation voltage brings about resolution of the components by CZE. Since the analytes have been concentrated their detection is far more accurate.

Preferably, the nature of the sol-gel/particle matrix is such that desorption of a high proportion of the analytes can occur efficiently with a minimum required volume of solvent. In one preferred embodiment, a capillary channel is employed, and the column is firmly positioned adjacent to (or anchored to) the wall of the capillary, enabling it to withstand repeated pressurization during sample application. In a second preferred embodiment, a microchannel channel is employed, and the column is applied to a chip or plate so as to form the desired microchannel. Preferably, the sol-gel matrix and chromatographic particles of such the devices of the present invention are selected to be chemically stable and to allow repeated, similar, adsorptions and desorptions of sample analytes so as to be multiply reusable. Alternatively, the columns of such devices may be designed for single-use analysis.

In preferred embodiments, the dimensions of the column will be no greater than about 5 mm in length, and will have an internal diameter in the range of from about 25 μm to about 360 μm. Larger or smaller columns may of course be employed. Preferably, the column size will be selected to that sufficient sorbent is present to provide a binding capacity for selected analytes which, when desorbed, permit adequate detectability and resolution for the analysis being investigated. While the present invention is particularly suitable for use in capillary zone electrophoresis, it will be appreciated that the solgel compositions and devices of the present invention may comprise columns of any diameter or length, and may include micro-bore or nano-bore columns suitable for use in a broad range of alternative analytical and preparative procedures (e.g., liquid chromatography (e.g., micro or nano liquid chromatography), capillary electrophoresis, capillary electrochromatography (CEC), reverse phase chromatography, ion-exchange chromatography, affinity chromatography, normal phase chromatography, enzymatic reaction, etc.).

The concentrating devices of the present invention may be used in the analysis of a wide range of biomolecules, including proteins and peptides, nucleic acid molecules, drugs, agricultural compounds, bacteria and viruses.

The use of the above-described sol-gel concentrating device facilitates analysis of low concentration samples. A subsequent injection of a small volume of eluting solvent rapidly removes the sample in a highly concentrated and often purified form. Manipulation of even the smallest samples is readily achieved via the conventional operation of the capillary electrophoresis system. Large samples volumes are readily accommodated since the analytes they contain are progressively concentrated on the mini column before being desorbed in a small volume of eluting solvent. Concentration of the sample can be achieved using pressure, vacuum or voltage.

The compositions and methods of the present invention are particularly suitable for use in automated or semi-automated capillary electrophoretic systems (for example in concert with the teachings of U.S. Pat. Nos. 6,001,230; 5,320,730, etc.). A particularly preferred such electrophoretic system includes a P/ACE MDQ (Beckman-Coulter) configured with a selectable-wavelength UVN is (for example, 200, 214, 254 and 280 nm) detector, UV source optics, a dual-wavelength laser-induced fluorescence detector, a 488 nm argon ion laser module, a temperature-controlled sample storage module, and 32 Karat™ Software (Beckman-Coulter) configured on an IBM personal computer.

The compositions and methods of the present invention are also particularly suitable for use in analytical methods that employ microchannels. Methods for forming and using microchannels are described by: Backhouse, C. J. et al. (2003) ("IMPROVED RESOLUTION WITH MICROCHIP-BASED ENHANCED FIELD INVERSION ELECTROPHORESIS, Electrophoresis 24(11):1777-1786), Bharadwaj, R. et al. (2002) ("DESIGN AND OPTIMIZATION OF ON-CHIP CAPILLARY ELECTROPHORESIS, Electrophoresis 23(16):2729-2744), Bromberg, A. et al. (2004) ("MULTICHANNEL HOMOGENEOUS IMMUNOASSAY FOR DETECTION OF 2,4,6-TRINITROTOLUENE (TNT) USING A MICROFABRICATED CAPILLARY ARRAY ELECTROPHORESIS CHIP, Electrophoresis 25(12):1895-1900), Chen, G. et al. (2004) ("FAST AND SIMPLE SAMPLE INTRODUCTION FOR CAPILLARY ELECTROPHORESIS MICROSYSTEMS, Analyst 129(6):507-511 (Epub 2004 Apr. 20)), Chen, S. H. et al. (2002) ("FLOW-THROUGH SAMPLING FOR ELECTROPHORESIS-BASED MICROCHIPS AND THEIR APPLICATIONS FOR PROTEIN ANALYSIS, Anal. Chem. 74(19):5146-5153), Doherty, E. A. et al. (2003) ("MICROCHANNEL WALL COATINGS FOR PROTEIN SEPARATIONS BY CAPILLARY AND CHIP ELECTROPHORESIS, Electrophoresis 24(1-2):34-54), Du, Y. et al. (2005) ("MICROCHIP CAPILLARY ELECTROPHORESIS WITH SOLID-STATE ELECTROCHEMILUMINESCENCE DETECTOR, Anal. Chem. 77(24): 7993-7997), Futterer, C. et al. (2004) ("INJECTION AND FLOW CONTROL SYSTEM FOR MICROCHANNELS, Lab Chip. 4(4):351-356 (Epub 2004 May 11)), Griffiths, S. K. et al. (2002) ("DESIGN AND ANALYSIS OF FOLDED CHANNELS FOR CHIP-BASED SEPARATIONS, Anal. Chem. 74(13):2960-2967), Hong, J. W. et al. (2001) ("MICROFABRICATED POLYMER CHIP FOR CAPILLARY GEL ELECTROPHORESIS, Biotechnol. Prog. 17(5):958-962), Jung, B. et al. (2006) ("ON-CHIP MILLIONFOLD SAMPLE STACKING USING TRANSIENT ISOTACHOPHORESIS, Anal. Chem. 78(7):2319-2327), Lee, G. B. et al. (2005) ("ON THE SURFACE MODIFICATION OF MICROCHANNELS FOR MICROCAPILLARY ELECTROPHORESIS CHIPS, Electrophoresis 26(24):4616-4624), Li, H. F. et al. (2004) ("A COMPACTLY INTEGRATED LASER-INDUCED FLUORESCENCE DETECTOR FOR MICROCHIP ELECTROPHORESIS, Electrophoresis 25(12):1907-1915), Li, M. W. et al. (2006) ("DESIGN AND CHARACTERIZATION OF POLY(DIMETHYLSILOXANE)-BASED VALVES FOR INTERFACING CONTINUOUS-FLOW SAMPLING TO MICROCHIP ELECTROPHORESIS, Anal Chem. 78(4):1042-1051), Lichtenberg, J. et al. (2002) ("A MICROCHIP ELECTROPHORESIS SYSTEM WITH INTEGRATED IN-PLANE ELECTRODES FOR CONTACTLESS CONDUCTIVITY DETECTION, Electrophoresis 23(21):3769-3780), Liu, J. et al. (2004) ("SURFACE-MODIFIED POLY(METHYL METHACRYLATE) CAPILLARY ELECTROPHORESIS MICROCHIPS FOR PROTEIN AND PEPTIDE ANALYSIS, Anal. Chem. 76(23):6948-6955), Liu, Y. et al. (2005) ("STACKING DUE TO IONIC TRANSPORT NUMBER MISMATCH DURING SAMPLE SWEEPING ON MICROCHIPS, Lab Chip 5(4):457-465 (Epub 2005 Mar. 7)), Pallandre, A. et al. (2006) ("SURFACE TREATMENT AND CHARACTERIZATION: PERSPECTIVES TO ELECTROPHORESIS AND LAB-ON-CHIPS, Electrophoresis 27(3):584-610), Petsev, D. N. et al. (2005) ("MICROCHANNEL PROTEIN SEPARATION BY ELECTRIC FIELD GRADIENT FOCUSING, Lab Chip 5(6):587-597 (Epub 2005 Apr. 15)), Richards, P. et al. (2002) ("FUNCTIONAL PROTEOMICS USING MICROCHANNEL PLATE DETECTORS," PROTEOMICS, 2(3):256-261), Rossier, J. et al. (2002) ("POLYMER MICROFLUIDIC CHIPS FOR ELECTROCHEMICAL AND BIOCHEMICAL ANALYSES, Electrophoresis 23(6):858-867), Scherer, J. R. Et Al. (2001) ("HIGH-PRESSURE GEL LOADER FOR CAPILLARY ARRAY ELECTROPHORESIS MICROCHANNEL PLATES, Biotechniques 31(5): 1150-1152, 1154), Wang, K. et al. (2006) ("MICROCHANNEL-ELECTRODE ALIGNMENT AND SEPARATION PARAMETERS COMPARISON IN MICROCHIP CAPILLARY ELECTROPHORESIS BY SCANNING ELECTROCHEMICAL MICROSCOPY, J. Chromatogr. A. 1110(1-2):222-226 (Epub 2006 Feb. 3)), and Xuan, X. et al. (2005) ("ACCELERATED PARTICLE ELECTROPHORETIC MOTION AND SEPARATION IN CONVERGING-DIVERGING MICROCHANNELS, Anal. Chem. 77(14): 4323-4328).

The compositions and methods of the present invention may be employed in concert with assay procedures (e.g., immunoassays, etc.; see U.S. Pat. No. 5,863,401) to permit the simultaneous analysis of multiple analytes. Likewise, the compositions and methods of the present invention may be employed for quantitating the concentration of protein components and of the total protein in fluids (see, U.S. Pat. No. 5,490,909).

In preferred embodiments, the concentrating devices of the present invention additionally desalt (i.e., remove some or all undesired salt from) the sample. In highly preferred embodiments, the concentrating device is adapted to achieve the simultaneous concentration of sample analytes and the desalting of the applied sample. In accordance with the present invention, a single concentrating device, or multiple devices (arranged in series or in parallel) may be employed.

The above-described sol-gel concentrating device provides multiple advantages over devices of the prior art. The sol-gel concentrating device of the present invention need not be attached to capillary pieces. Nitric acid may be employed instead of hydrochloric acid. The use of nitric acid is preferred since hydrochloric acid dissolves silica, unlike nitric acid. The use of 0.1 M HCl has the added disadvantage of not reducing the pH as much as nitric acid, thereby resulting in only an incomplete hydrolysis prior to polycondensation to give a mechanically weak matrix. In contrast, the matrix formed by the present invention can withstand substantial pressure (e.g., 2000 psi or more). Additionally, the sol-gel concentrating device of the present invention uses less ethanol and more particles than prior art devices. Such attributes make the sol-gel monolith of the present invention less susceptible to cracks and fissures. The use of bare silica can be avoided by the present invention (thereby avoiding problems with basic compounds such as the irreversible adsorption of basic proteins and peptides). Further, the use of a step-wise heating process advantageously secure the monolith and avoids the formation of discontinuous pieces.

Having now generally described the invention, the same will be more readily understood through reference to the following examples, which are provided by way of illustration and are not intended to be limiting of the present invention unless specified.

EXAMPLE 1

CZE Analysis Using Preferred Concentrating Device

A column concentrating device is formulated in accordance with the principles of the present invention. The column is prepared from capillary tubes having internal diameters of 25-360 μm. The column materials are: tetraethylorthosilicate (200 μl), Ethanol (156 μl), 1.0 M nitric acid (258 μl), and chromatography particles of varying size and pore volume (e.g., 455 mg of 5 μm Ultrasphere® particles (Beckman Coulter, Inc.).

The following column filling process is employed: Dissolve 200 μl of tetraethylorthosilicate in 156 μl of ethanol by vortexing briefly. Then add 258 μl of 1.0 M nitric acid and vortex until the solution is clear and uniform. Slowly add particles and vortex carefully to mix particles with the solution until all the particles are properly wet. Sonicate the slurry briefly to remove trapped air around the particles. Insert capillaries through a Teflon® septum into the vial containing the slurry until the end of the capillary is submerged in the slurry. Apply about 20 lbs/in$^2$ (psi) of pressure using a nitrogen tank regulator until about 5-10 cm of the capillary has been filled with the slurry.

The silicate sol-gel is formed using the following heating process: Lay all capillaries flat on a tray in an oven. Incubate the capillaries at room temperature (25° C.) for 1.0 h, then heat the capillary tube according to the following heating program: 400° C. for 16-18 hours, then 50° C. for 1.0 hour, then 70° C. for 16-18 hours, then 100° C. for 1 hour, and then 120° C. for 2 hours.

Figure 2:
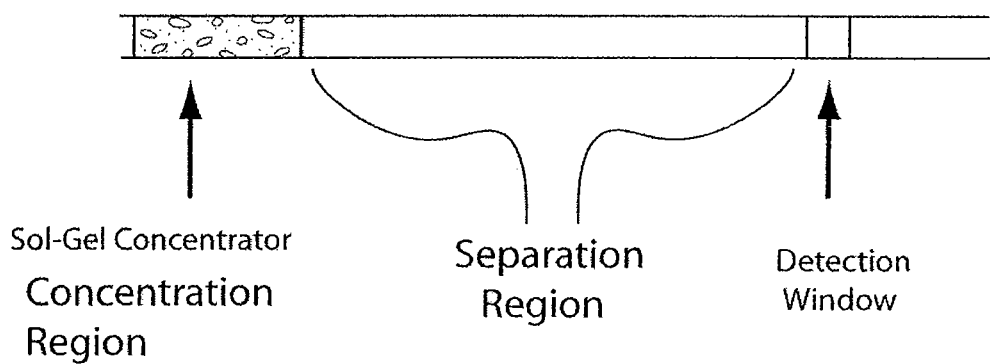
FIG. 2 illustrates a concentration device of the present invention.
Figure 3:
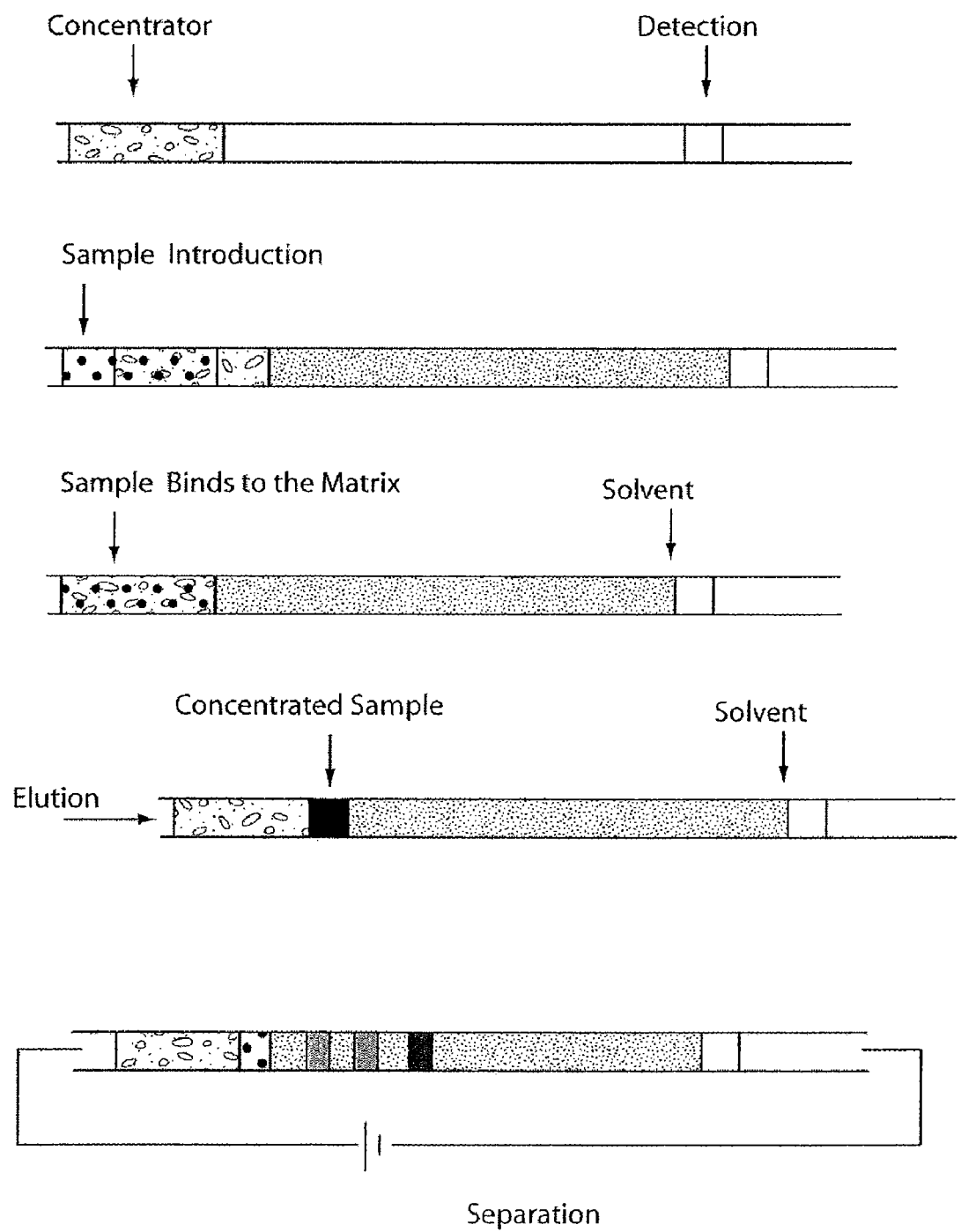
FIG. 3 illustrates the process of analyte concentration, elution and separation using a concentration device of the present invention.

FIG. 2 illustrates a concentrating device of the present invention. FIG. 3 illustrates the process of analyte concentration, elution and separation using a concentration device of the present invention. As shown in FIG. 3, a concentrating device (concentrator) is provided in a capillary tube containing a desired CZE matrix. Sample is introduced and permitted to bind to the matrix of the concentrating device. Washing with elution buffer results in a concentrating of the sample. Application of an electric field results in electrophoresis and separation of the sample analytes.

Figure 4:
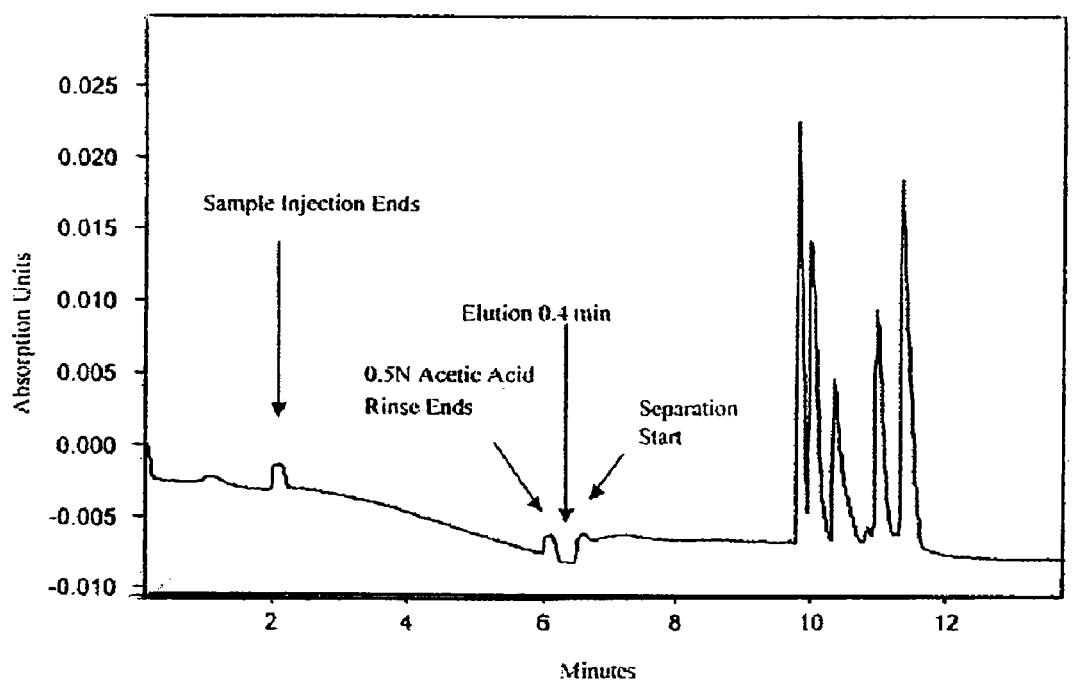
FIG. 4 illustrates the resolution of a sample using CZE.

FIG. 4 illustrates the separation profile obtained using a concentrating device of the present invention.

Figure 5A:
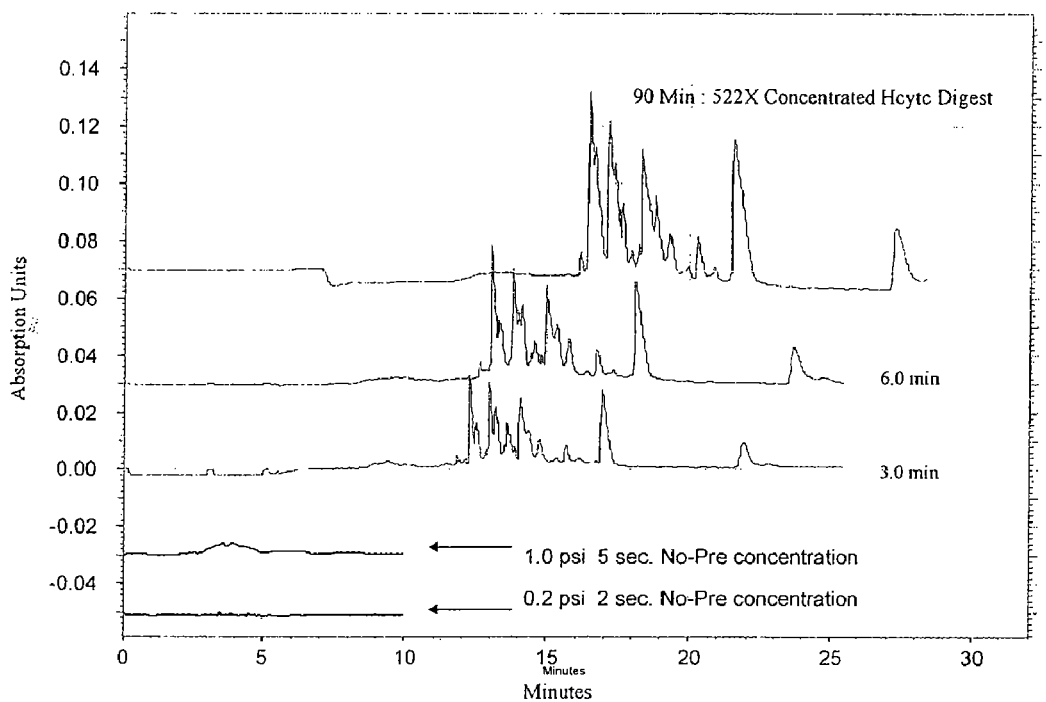
FIG. 5A shows the enhanced separation obtained through the use of the present invention.
Figure 5B:
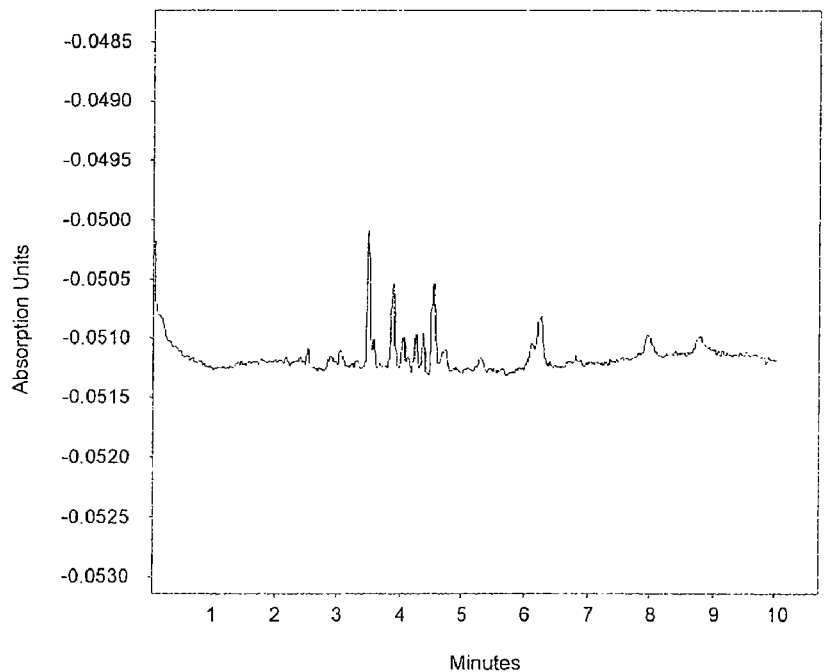
FIG. 5B shows the capacity of the invention to separate peaks of the horse cytochrome C (Hcytc) digest even at concentrations as low as 8000 picomol/ml.

FIG. 5A shows the enhanced separation obtained through the use of the present invention. As shown in FIG. 5A, no useful separation of horse heart cytochrome C (Hcytc) digest is obtained in the absence of pre-concentration (0.2 psi for 2 seconds, or 1.0 psi for 5 seconds). Concentration for 3, 6, or 9 minutes at 50 psi yielded on a 0.5 cm ultrasphere (Beckman Coulter, Inc.) sol-gel plug increasingly better resolved peaks. FIG. 5B shows the capacity of the invention to separate peaks of the Hcytc digest even at concentrations as low as 8000 picomol/ml.

FIG. 6 shows the ability of the concentrating devices of the present invention to separate digest products of sheep cytochrome C (ShCytc) and pig cytochrome C (PcCytc), consisting of identical amino acid sequences). As shown in FIG. 6, 2 minute pre-concentration with a concentrating device of the present invention permitted the detection of the separated peptide fragments, under conditions in which the separation of non-concentrated materials could not be detected.

FIG. 7 shows the reproducibility of analyte separation using the concentrating devices of the present invention. Shown are the separation profiles for Hcytc reduced and alkylated before digestion. The capillary contained a 0.5 cm plug of 5μ/sol-gel in 75μ capillary. Electrophoresis voltage was 167 v/cm, 5 kv. Sample was loaded in 0.5 M acetic acid, and was eluted in 60% acetonitrile (ACN) in loading buffer.

FIG. 8 shows the reproducibility of analyses of digests of Hcytc (7 pmole/μ; run 76-91; sample application: 0.4 min at 25 psi).

FIG. 9 shows the ability of the methods and apparatus of the present invention to separate peptide digestion products of yeast hexokinase. The yeast hexokinase preparation (5 femtomole/μl) was concentrated on a solgel concentrator for detection of absorption at 200 nm. FIG. 10 shows the reproducibility of multiple analyses of digests of yeast hexokinase (10 nanomole/μl; run 2-10, sample application: 0.4 min at 25 psi).

FIG. 11 illustrates the extreme sensitivity of the detection obtainable using devices of the present invention. A bovine hexokinase (52 kDa MW; 50 fentomoles (fmoles)) digest was concentrated using a sol-gel capillary for different time intervals. Trace A shows the electroferogram for 0.2 picomoles (pmoles) injected and 1.0 pmoles/μl eluted. Trace B shows the electroferogram for 6.25 pmoles injected and 89 fmoles/μl eluted. Trace C shows the electroferogram for 1.25 fmoles injected and 17.8 fmoles/μl eluted.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for forming a concentrating device, the method comprising:
   a) filling a tube with a composition comprising an alkylsilicate material, a solvent, and particles;
   b) heating the composition in a step-wise manner at temperatures less than about 60° C. to the composition to accelerate polymerization of the slurry;
   c) heating the composition from b) at a temperature less than about 80° C. to evaporate the solvent; and
   d) curing the heated alkylsilicate material of the heated composition from c) at a temperature of less than about 130° C.

2. The method of claim 1 wherein in step b), the composition is heated to between about 35-45° C., and then to between about 45-55° C.

3. The method of claim 2 wherein in step c), the heated composition is further heated to between about 60-80° C.

4. The method of claim 3 wherein in step c), the heated composition is further heated to between 60-80° C. for about 16-18 hours.

5. The method of claim 3 wherein in step d), the heated composition from c) is further heated between 90-130° C.

6. The method of claim 3 wherein in step d), the heated composition from c) is further heated in a two step heating process.

7. The method of claim 1 wherein in step d) the heated composition from c) is initially heated from 90-110° C., and then to 110-130° C.

8. The method of claim 1 wherein the tube is a capillary tube.

9. The method of claim 1 wherein the solvent comprises an organic solvent.

10. The method of claim 1 wherein the alkylsilicate material comprises tetraethylorthosilicate.

11. The method of claim 1 wherein the particles are chromatography particles.

12. The method of claim 1 wherein the solvent comprises methanol.

13. The method of claim 1 wherein the concentrating device is a capillary zone electrophoresis device.

14. The method of claim 1 wherein b), c), and d) are performed in an oven.

15. The method of claim 1 wherein a) comprises inserting the tube into a container containing the composition.

16. The method of claim 1 wherein the composition further comprises an acid.

17. The method of claim 1 wherein the composition further comprises nitric acid.

18. The method of claim 1 wherein the cured heated composition from d) withstands 2000 psi without breaking.

19. The method of claim 1 wherein the cured heated composition from d) is free of cracks and fissures.

20. The method of claim 1 wherein the particles in the composition are coated with silane.

21. A concentrating device made by the process of claim 1.

* * * * *

UNITED STATES PATENT AND TRADEMARK OFFICE
CERTIFICATE OF CORRECTION

PATENT NO. : 8,182,730 B2  
APPLICATION NO. : 12/185999  
DATED : May 22, 2012  
INVENTOR(S) : Chitra Kumari Ratnayake et al.

Page 1 of 1

It is certified that error appears in the above-identified patent and that said Letters Patent is hereby corrected as shown below:

On the Title Page

Please add the Assignee, Item (73), as indicated below:
Beckman Coulter, Inc., Brea, CA (US)

Signed and Sealed this
Twenty-third Day of April, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,182,730 B2 | |
| APPLICATION NO. | : 12/185999 | |
| DATED | : May 22, 2012 | |
| INVENTOR(S) | : Chitra Kumari Ratnayake et al. | |

It is certified that error appears in the above-identified patent and that said Letters Patent is hereby corrected as shown below:

In the Claims

Cancel claim 21 at column 16, line 27.

Signed and Sealed this
Sixteenth Day of June, 2015

Michelle K. Lee
*Director of the United States Patent and Trademark Office*